Figure 1:
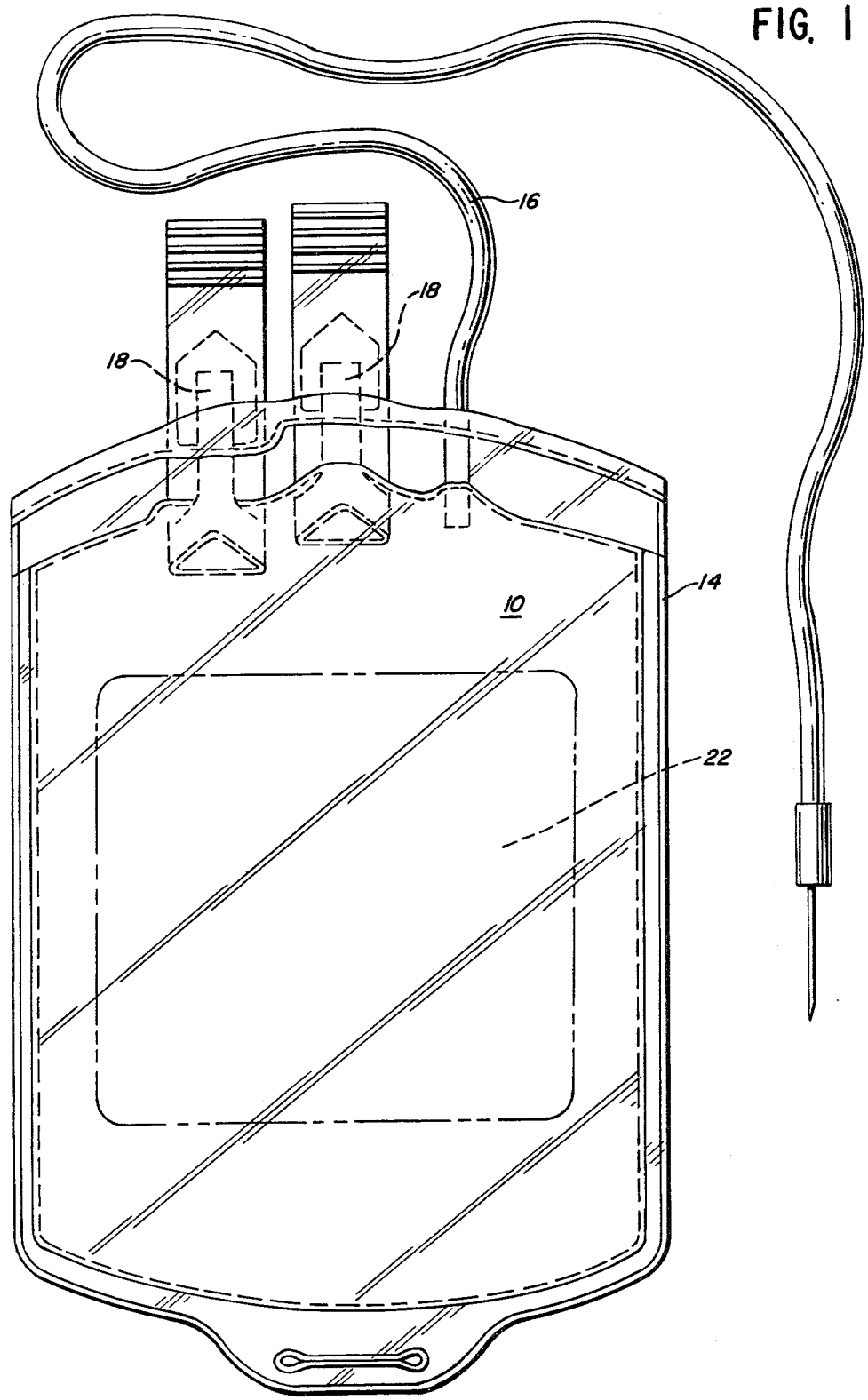

United States Patent [19]

Gajewski et al.

[11] 4,286,597

[45] Sep. 1, 1981

[54] BLOOD COMPATIBLE POLYMERS AND MEDICAL DEVICES MADE THEREFROM CONTAINING DIOCTYLADIPATE PLASTICIZER

[75] Inventors: Henry M. Gajewski, Winnetka; Gerald A. Grode, Grayslake; Paul E. Measells, Libertyville; Jeffrey E. Miripol, Evanston, all of Ill.

[73] Assignee: Baxter Travenol Laboratories, Inc., Deerfield, Ill.

[21] Appl. No.: 142,290

[22] Filed: Apr. 21, 1980

Related U.S. Application Data

[63] Continuation of Ser. No. 954,970, Oct. 26, 1978, abandoned.

[51] Int. Cl.$^3$ .......................... A61M 5/00; A61J 1/00
[52] U.S. Cl. ............................. 128/272; 128/214 D
[58] Field of Search ............. 128/214 D, 214 R, 272, 128/DIG. 24; 260/31.8 XA, 31.8 P, 31.8R

[56] References Cited

U.S. PATENT DOCUMENTS 3,064,647  11/1962  Earl .................................. 128/214 D
3,186,961  6/1965  Sears et al. ...................... 260/31.8 R

*Primary Examiner*—Stephen C. Pellegrino
*Assistant Examiner*—T. J. Wallen
*Attorney, Agent, or Firm*—Paul Flattery; John A. Caruso; Q. Todd Dickinson

[57] ABSTRACT

Blood-compatible, chlorine-free polymers such as a flexible, non-toxic, sterilizable polyester plastic formulation may contain from 5 to 70 percent by weight of a blood-extractable plasticizer such as di-2-ethylhexyladipate, to cause blood which is stored in contact with the polymer to exhibit a surprisingly low hemolysis rate when compared with corresponding polymers which are free of the plasticizer. Accordingly, blood bags, tubing and other medical blood-contacting devices may be advantageously made from these polymers.

6 Claims, 1 Drawing Figure

BLOOD COMPATIBLE POLYMERS AND MEDICAL DEVICES MADE THEREFROM CONTAINING DIOCTYLADIPATE PLASTICIZER

CROSS-REFERENCE TO RELATED APPLICATION

This application is a continuation of U.S. Application Ser. No. 954,970, filed Oct. 26, 1978, now abandoned.

BACKGROUND OF THE INVENTION

Multiple blood bags are commercially available from the Fenwal Division of Baxter Travenol Laboratories, Inc. for collecting and processing blood under sterile conditions, to obtain various blood components that may be desired, for example, packed red cells, plasma, platelets, and cryoprecipitate.

The currently-available blood bags are made of a polyvinyl chloride formulation which includes, as an ester-type plasticizer, di-2-ethylhexylphthalate. Such a plasticizer is absolutely necessary for polyvinyl chloride formulations, since polyvinyl chloride itself is not a suitable flexible plastic material for use as a container. Such blood bags have served extremely well in the storage and processing of blood and blood components, exhibiting a high survival rate with a low plasma hemoglobin content after, for example, 21 days of storage.

Other chlorine-free plastic formulations have been tested as candidate blood bag materials as well, including flexible polyesters, polyolefins, and the like. Surprisingly, many of the materials tested, while giving indications of being good plastic materials for the manufacture of blood bags, have caused blood stored in containers made of such materials under the usual blood storage conditions to exhibit an undesirably high plasma hemoglobin content after, for example, 21 days of storage, indicating that the lysis rate of the red blood cells is high.

In accordance with this invention, it has been surprisingly found that the presence of certain ester-type plasticizers such as di-2-ethylhexylphthalate and di-2-ethylhexyladipate in various chlorine-free plastics which do not normally contain such plasticizers causes a significant lowering of the plasma hemoglobin content during long-term storage of blood in containers made of such plastic, when compared with containers made of similar plastic materials which are free of the ester-type plasticizers. This can be used to provide blood bags and other blood-contacting medical devices which are made out of chlorine-free plastic entities, having different advantages and properties as may be desired, but which nevertheless exhibit a similar desirably low blood hemolysis rate during long-term storage to that presently available in commercial polyvinyl chloride formulations.

DESCRIPTION OF THE INVENTION

In accordance with this invention, a blood bag or the like may be provided which comprises a sealed, flexible, translucent container equipped with access tubing and sealed access ports. The blood bag comprises a flexible, hemocompatible, sterilizable halogen-free plastic formulation which preferably contains from 5 to 70 percent by weight of a blood-extractable plasticizer comprising a dioctyladipate.

It is specifically desirable for the concentration and distribution of plasticizer in the bag to be such that when the bag is filled with blood and stored on a long-term basis, the concentration of the blood-extractable plasticizer in the blood rises to typically about 30 to 100 micrograms per ml., and preferably from 50 to 80 micrograms per ml., in the blood over 21 days. This takes place due to the extraction of the plasticizer from the plastic material in dissolved form into the blood.

It has been found to be difficult to dissolve the blood-extractable plasticizers used herein in bulk in the blood. It is found that a greater beneficial effect is provided by placing the extractable plasticizer in the plastic material of the blood bag for extraction by the blood during the storage.

If desired, only portions of the bag materials which are in contact with the blood contained therein may contain the blood-extractable plasticizers of this invention, although preferably the entire bag material contains the plasticizer. Alternatively, a plastic insert member such as a sheet of plastic, plastic beads, or the like may be positioned within the blood bag and may contain the blood-extractable plasticizer material, while the actual bag walls may be relatively free of plasticizer. Both of these circumstances are generally equivalent to the preferred use of blood-extractable plasticizer throughout essentially the entire material of the bag.

Preferably, the blood-extractable plasticizer used herein may be a branched octyladipate, and particularly, di-2-ethylhexyladipate. The blood-extractable plasticizer is preferably present in a concentration in the flexible bag wall of 5 to 50 weight percent and typically about 15 to 40 weight percent.

When a plastic insert is used, the concentration of the blood-extractable plasticizer in the insert may be increased up to about 70 percent if desired, since the insert is usually not a structural element and does not have to have a high tensile strength.

The use of the above described blood bag can result in a substantial reduction in plasma hemoglobin produced by blood stored under normal conditions for 21 days therein, when compared with blood in a corresponding, extractable plasticizer-free bag, stored under equivalent conditions.

If desired, the formulations of this invention may be used to make medical tubing and other devices.

The materials used in this invention may optionally be a polyester material containing the extractable plasticizer in the desired quantity. The polyester material may be made in accordance with the teachings of U.S. Pat. No. 4,045,431.

It may be desirable to incorporate the blood bag of this invention into a multiple bag system containing a plurality of blood bags connected by tubing, in which the additional blood bags may be of similar or different construction from the bag of this invention.

Alternatively, the compositions of this invention, and the resulting bags and medical tubing and similar devices made therefrom, may comprise other halogen-free plastic materials, plasticized as described above and with a blood-extractable plasticizer such as di-2-ethylhexyladipate. Candidate polymer materials for this purpose include non-toxic polyurethanes, polyamide materials such as nylon, polycarbonates, polysulfones, polyacrylates, polyvinylacetate and copolymers thereof with other vinyl polymer materials such as ethylene, polyacrylates, (particularly those of a hydrophilic nature such as hydroxylated polyacrylates), and other plastic materials which are sufficiently compatible with the blood-extractable plasticizer used to permit the formation of a stable, solid solution or dispersion of the blood-extractable plasticizer in the polymer material.

Referring to the drawings, FIG. 1 is a plan view of a blood bag made in accordance with this invention.

Blood bag 10 may be made of conventional construction, including a pair of plastic sheets sealed at periphery 14 and containing a blood collection tube 16 (which may also be made of the composition of this invention) having the usual donor needle, and a pair of sealed access ports 18.

In accordance with this invention, bag 10 is made of a transparent, flexible, sterilizable and preferably autoclavable material which contains preferably about 20 to 30 percent by weight of a blood-extractable plasticizer, such as di-2-ethylhexyladipate. Specifically, the plastic material which contains the blood-extractable plasticizer may be the polyester formulation described above. Such blood bags, which may contain about 20 percent by weight of blood-extractable plasticizer, can cause a substantial reduction in the plasma hemoglobin of blood stored under normal conditions for 21 days in the blood bag, when compared with the corresponding extractable plasticizer-free blood bag made of the same polyester material in which the blood is collected in the bag and stored under equivalent conditions. Such blood bags may be made by soaking the bags in the liquid, blood-extractable plasticizer.

If desired an optional plastic insert 22 may be inserted within the bag 10. Insert 22 may be made of a similar material to the bag 10, or a different plastic material which is compatible with the desired blood-extractable plasticizer used herein. Accordingly, the material of bag 10 may be relatively free of the desired blood-extractable plasticizer, but insert 22 within the bag may carry any desired amount of the plasticizer, preferably from 15 to 70 percent by weight, to provide the extractable plasticizer to the blood which is placed in bag 10. It has been found that the desirable results of this invention can be achieved by this alternate technique.

Insert 22 may be a single sheet, or a plurality of plastic beads, or any other convenient structure. For example, in this particular alternate instance, blood bag 10 may be made out of a flexible, collapsible plastic material which is generally free of blood-extractable plasticizers, or optionally it may contain such plasticizers as desired. Specific plastic materials with which the blood bag may be made in this instance include the polymers listed above, plus polyolefins such as polyethylene, polypropylene, or polyolefin block copolymer formulations as specifically described in U.S. Patent Application Ser. No. 819,924, filed July 28, 1977 now U.S. Pat. No. 4,140,162.

Insert 22, on the other hand, may be made of a blood-compatible plastic material including any of the above-listed polymers, for example, a blood-compatible polyvinylchloride formulation which may contain preferably up to about 50 percent di-2-ethylhexyladipate, to be extracted into the blood over the storage period, for example, 28 percent by weight. If desired, higher concentrations than 50 percent of the extractable plasticizer may be placed in insert 22, since there is no need for insert 22 to exhibit a high tensile strength, as would be necessary if it were part of the bag wall itself.

Bag 10 may contain an appropriate blood preservative 30 such as ACD or CPD solution, as is conventional for storage of the blood. During storage, the presence of the plasticizer effectively suppresses the amount of plasma hemoglobin which is generated over a period of time, compared with blood stored in a bag made of an extractable plasticizer-free plastic formulation. Accordingly, the above described halogen-free plastic formulations may, for the first time, be formulated into blood bags and other medical devices for long-term contact with blood, while at the same time exhibiting an unexpectedly low red cell hemolysis rate, when compared with the corresponding plasticizer-free plastic formulations.

If desired, blood bag 10 may be equipped with a sterile connector device, for example that shown in U.S. Pat. No. 4,004,486, or any other sterile connector system, so that the bag may be connected together with other blood bags or sterile equipment without breaching the sterility of the system.

The above has been offered for illustrative purposes only, and is not intended to limit the invention of this application, which is as defined in the claims below.

That which is claimed is:

1. The method of storing blood which comprises placing said blood for a period of days into a flexible, hemocompatible, sterilizable, chlorine-free plastic material which contains sufficient dioctyladipate to cause a reduced plasma hemoglobin content of blood stored in contact therewith for 21 days, when compared with blood stored in contact with the same blood compatible material free of dioctyladipate.

2. The method of claim 1 in which said dioctyladipate contains branched octyl groups.

3. The method of claim 2 in which said dioctyladipate is di-2-ethylhexyladipate.

4. The method of claim 1 in which said chlorine-free plastic material contains from 5 to 50 percent by weight of said dioctyladipate.

5. The method of claim 4 in which from 15 to 40 percent by weight of said dioctyladipate is present.

6. The method of claim 1 in which said chlorine-free plastic material is a polyester.

* * * * *